United States Patent [19]

Young et al.

[11] 4,431,845
[45] Feb. 14, 1984

[54] METHOD FOR THE PREPARATION OF 1-HYDROXYL-TERMINATED POLY(HALOALKYLENE ETHERS)

[75] Inventors: Chung I. Young, Roseville; Loren L. Barber, Jr., Woodbury, both of Minn.

[73] Assignee: Minnesota Mining and Manufacturing Company, St. Paul, Minn.

[21] Appl. No.: 355,179

[22] Filed: Mar. 5, 1982

Related U.S. Application Data

[62] Division of Ser. No. 213,118, Dec. 4, 1980, abandoned.

[51] Int. Cl.³ .................... C07C 41/02; C07C 41/03

[52] U.S. Cl. ...................................... 568/606; 568/607; 568/611; 568/614; 568/615; 568/659; 568/660; 568/661; 568/662; 568/663; 568/669; 568/670; 568/674; 568/676; 568/677; 568/681; 568/683; 568/684; 252/182

[58] Field of Search ............... 568/606, 607, 611, 614, 568/615, 659–663, 669–670, 674, 676, 677, 681, 683–684; 252/182

[56] References Cited

FOREIGN PATENT DOCUMENTS 2919834  11/1979  Fed. Rep. of Germany ...... 568/614

*Primary Examiner*—Howard T. Mars
*Attorney, Agent, or Firm*—Donald M. Sell; James A. Smith; James V. Lilly

[57] ABSTRACT

A method for the preparation of hydroxyl-terminated poly(haloalkylene ethers) is disclosed wherein a catalyst system comprising a fluorinated acid and a polyvalent tin compound is utilized.

8 Claims, No Drawings

METHOD FOR THE PREPARATION OF 1-HYDROXYL-TERMINATED POLY(HALOALKYLENE ETHERS)

CROSS-REFERENCE TO RELATED APPLICATION

This is a division of Application Ser. No. 213,118 filed Dec. 4, 1980, abandoned, which was a continuation of Application Ser. No. 76,557 filed Sept. 18, 1979, abandoned, which was a continuation-in-part of Application Ser. No. 906,744 filed May 17, 1978, abandoned.

BACKGROUND OF THE INVENTION

Field of the Invention

This invention is related to hydroxyl-terminated poly(haloalkylene ethers). More particularly it is related to hydroxyl-terminated poly(haloalkylene ethers) wherein the halogen atoms are preferably bromine or chlorine, processes for their preparation and novel catalyst systems useful in said processes. In the case of hydroxyl terminated poly(chloroalkylene ethers) the products are substantially colorless.

For the purposes of convenience, the hydroxyl-terminated poly(haloalkylene ethers) are sometimes referred to hereinafter as polyols. For purposes of this disclosure, the term "polyols" includes materials which have at least one terminal hydroxyl group.

DESCRIPTION OF THE PRIOR ART

Hydroxyl-terminated poly(haloalkylene ethers) and processes for their preparation are known. Frequently the processes utilize cationic polymerization techniques wherein oxirane monomers (e.g., alkylene oxides), alcohols and acid catalysts are employed to synthesize hydroxyl-functional prepolymers. Thus, for example, see U.S. Pat. Nos. 3,850,856; 3,910,878; 3,910,879; and 3,980,579.

The products described in these patents have not proven entirely satisfactory. For example, it has been found very difficult to control the temperature of the polymerization during their preparation. Additionally the chloroalkylene products are dark in color and tend to be very slow to react with various materials such as isocyanates unless substantial quantities of catalysts are employed therewith. Furthermore these products have been found to be unstable upon exposure to light (e.g., sunlight) and heat (e.g., temperatures above 50° C.). Thus they become even darker in color and increase in acidity and water content when exposed to such conditions. Still further the hydroxyl-terminated materials described in U.S. Pat. No. 3,980,579 adversely affect the catalytic activity of amine catalysts utilized in the preparation of polyurethane foam.

Other techniques for the preparations of hydroxyl-terminated poly(haloalkylene) ethers are also known. Thus U.S. Pat. No. 3,450,774 teaches the preparation of polymers having hydroxyl end groups by the cleavage of high molecular weight crystalline poly(epihalohydrin) in the presence of certain alkali compounds. The resulting polymers are crystalline and have low molecular weight. Moreover these polymers are only partially hydroxyl functional. Thus they may have carbonyl and ethynyl end groups in place of the hydroxyl end groups.

Other poly(haloalkylene ethers) are described in U.S. Pat. Nos. 3,636,163 and 3,850,857. The former patent describes the reaction of epibromohydrin and a phosphorous compound in the presence of a Friedel-Crafts catalyst. The latter patent describes the polymerization of epihalohydrin in the presence of a catalyst of a trialkyl onium salt of $HMF_6$ wherein M is a Group V element.

The present invention provides novel hydroxyl-terminated poly(haloalkylene ethers), processes for the preparation of the polyols and catalyst systems useful therein. The chloroalkylene ethers of the present invention represent a preferred class of materials. They are optically clear and colorless (e.g., they appear to have the same optical clarity as distilled water). Thus they exhibit a color magnitude (described more fully hereinafter) of less than about 10. Moreover, they are stable to the affects of heat and light (i.e., they resist degradation due to such conditions). Moreover, they possess excellent chemical reactivity towards isocyanate materials.

The colorless hydroxyl-terminated poly(chloroalkylene ethers) of the present invention are particularly useful where the color of the finished product is important (e.g., where the true color of the product is critical). Thus, for example, these materials are particularly useful in the preparation of cast urethane systems which can be used for such things as flooring materials, coatings and adhesives. Moreover the urethanes produced with the materials of the invention have been found to exhibit improved properties over prior art urethanes. Thus, for example, such urethanes exhibit excellent resistance to grease and oil.

SUMMARY OF THE INVENTION

In accordance with the present invention there are provided novel amorphous hydroxyl-terminated poly(haloalkylene ethers) having the formula

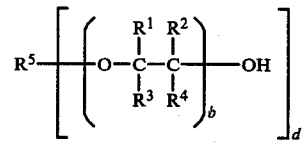

wherein $R^1$ and $R^2$ are each selected from hydrogen and methyl; $R^3$ and $R^4$ are each selected from hydrogen, lower alkyl groups containing from about 1 to about 10 carbon atoms, and lower haloalkyl groups containing from about 1 to 2 carbon atoms and from 1 to about 5 halogen atoms, provided that at least one of $R^3$ and $R^4$ is said lower haloalkyl group; $R^5$ is the residue of an organic hydroxyl material which hydroxyl material contained from 1 to about 6 hydroxyl groups; b is an integer of from 1 to about 50; and d is an integer of from 1 to about 6.

Preferably the polyols of the invention are poly(bromoalkylene ethers) or poly(chloroalkylene ethers). The poly(chloroalkylene ethers) preferably contain from about 20% to 60% by weight chlorine.

The poly(haloalkylene ether) polyols of the present invention are amorphous materials, that is, they do not exhibit a melting point. Moreover they may be either low molecular weight (i.e., about 250 MW) or high molecular weight materials (i.e., about 5000 MW) based upon the average hydroxyl functionality of the polyols. Additionally, the poly(chloroalkylene ether) polyols are substantially colorless. Thus they have a color magnitude of less than about 10.

There are also provided herein novel catalyst systems. These catalyst systems are useful in the preparation of the novel polyols and comprise (i) a fluorinated acid selected from the group consisting of bis(fluorinated aliphatic sulfonyl) alkanes, HF and acids of the formula $H_mXF_{n+m}$ wherein X is selected from the group consisting of boron, phosphorous, arsenic and antimony, m is 0 or 1 and n is 3 when X is boron and n is 5 when X is phosphorous, arsenic and antimony; and (ii) a polyvalent tin compound having the formula

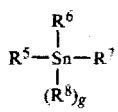

wherein g is 0 or 1;

$R^5$ and $R^6$ are the same or different and are selected from saturated and unsaturated aliphatic and aromatic hydrocarbyl groups containing from 1 to about 10 carbon atoms;

$R^7$ is selected from the group consisting of oxygen and saturated and unsaturated aliphatic and aromatic hydrocarbyl groups containing from 1 to about 10 carbon atoms, provided that when $R^7$ is oxygen then g is 0; and $R^8$ is selected from the group consisting of fluorine, acyloxy groups containing less than about 10 carbon atoms, saturated aliphatic hydrocarbyl groups containing from 1 to about 10 carbon atoms and

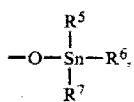

provided that when $R^5$, $R^6$ and $R^7$ are each saturated aliphatic hydrocarbyl groups then $R^8$ is selected from the group consisting of fluorine, acyloxy groups containing less than about 10 carbon atoms and

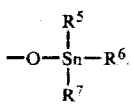

The molar ratio of the polyvalent tin compound to the fluorinated acid in the catalyst system is dependent upon the particular acid utilized. Thus, for example, the ratio of the tin compound to the bis(fluorinated aliphatic sulfonyl) alkane is in the range of about 0.2:1 to 2:1. Preferably the ratio is in the range of about 0.4:1 to .5:1.

The ratio of the tin compound to either the HF or the fluorinated acids of the formula $H_mXF_{n+m}$ is in the range of about 1.13:1 to 3:1. Preferably this ratio is in the range of about 1.2:1 to 2:1.

Still further there is provided a method of making the polyols of the invention utilizing the novel catalyst system wherein a hydroxyl containing material having from 1 to 6 hydroxyl groups is combined with an alkylene oxide and polymerized in the presence of the above-described catalyst system.

DETAILED DESCRIPTION OF THE INVENTION

The hydroxyl-terminated poly(haloalkylene ethers) of the invention are prepared by combining a hydroxyl-containing material, an alkylene oxide (at least about 50% by weight of which is a haloalkylene oxide) and the catalyst system of the invention and polymerizing the resultant mixture. Polymerization may be carried out at a temperature in the range of about 0° C. to 110° C. Preferably polymerization is carried out at a temperature in the range of about 40° C. to 80° C.

Solvents may also be employed in the polymerization mixture. They are especially useful when one or more of the ingredients of the mixture is a solid. Suitable solvents solvate (but are otherwise inert to) the materials in the mixture. Representative examples of suitable solvents are benzene, toluene, methylene chloride, carbon tetrachloride and 1,2-dichloroethane.

Although the polymerization proceeds smoothly to completion, there may be some unpolymerized haloalkylene oxide left. This material may be separated from the poly(haloalkylene ethers) of the invention by warming the polymerization mixture (e.g., to about 80° C.) and subjecting the heated mixture to reduced pressure (e.g., about 0.01 Torr) for a short period of time (e.g., about 1-2 hours).

A wide variety of hydroxyl-containing materials are useful in the present invention. They include, for example, water and liquid and solid organic materials which have a hydroxyl functionality of at least one. The organic materials may be monomeric or polymeric and are preferably selected from mono-and polyhydric alkanols, haloalkanols and polymeric polyols.

The hydroxyl groups of the organic materials may be terminal or pendant (i.e., other than terminal) groups. Hydroxyl-containing materials containing both terminal and pendant hydroxyl groups may also be used. The molecular weight of the organic hydroxyl-containing material may vary over a rather wide range. For example it may be in the range of from about 10 to about 2,500.

Preferably, the organic hydroxyl-containing material is an aliphatic material which contains at least one primary or secondary aliphatic hydroxyl group (i.e., the hydroxyl group is bonded directly to a non-aromatic carbon atom). Most preferably said organic material is an alkane polyol.

Mono- and polyhydric alkanols useful in the present invention include methanol, ethanol, isopropanol, 2-butanol, 1-octanol, octadecanol, 3-methyl-2-butanol, 5-propyl-3-hexanol, cyclohexanol, ethylene glycol, propylene glycol, 1,3-butanediol, 1,4-butanediol, 1,6-hexanediol, 1,4-cyclohexanedimethanol, glycerol and sorbitol.

Mono- and polyhydric haloalkanols useful in the predent invention include 2-chloroethanol, 3-chloropropanol, 2,3-dichloropropanol, 3,4-dibromo-1,2-butanediol, 2,3-dibromo-1,4-butanediol, 1,2,5,6-tetrabromohexane-3,4-diol.

Polymeric hydroxyl-containing materials useful in the present invention include polyoxyethylene and polyoxypropylene glycols and triols of molecular weights from about 200 to about 2000 (corresponding to hydroxyl equivalent weights of 100 to 1000 for the diols and 70 to 630 for triols); hydroxy-terminated polyalkadienes; and polytetramethylene glycols of varying molecular weight such as the Polymeg ® series of glycols available from Quaker Oats Company as Polymeg ® 650, 1000 and 2000.

The foregoing list of useful hydroxyl-containing materials is intended to be illustrative only. Still other hydroxyl-containing materials are also useful as will be clear as a result of this disclosure.

The exact hydroxyl-containing material selected for use in the present invention is dependent upon the terminal hydroxyl functionality desired in the poly(chloroalkylene ether) polyol. It has been found that the polyols of the invention have the same hydroxyl functionality as that of said hydroxyl-containing starting material and that the hydroxyl-functionality is present as a terminal hydroxyl group. Thus, for example, when a monofunctional hydroxyl-containing material is used, a monohydric polyether is obtained; when difunctional hydroxyl-containing materials are used; when dihydric polyether polyols are obtained; etc.

Mixtures of hydroxyl-containing compounds may be used if desired. For example, one may use mixtures of two or more poly-functional hydroxyl compounds, one or more mono-functional hydroxyl compounds with one or more polyfunctional hydroxyl compounds, etc.

A wide variety of haloalkylene oxides are useful in the present invention. They include, for example, epichlorohydrin, epibromohydrin, 1-chloro-2-methyl-2,3-epoxypropane, 1,4-dibromo-2,3-epoxybutane, 1,4-dichloro-2,3-epoxybutane, 1-bromo-2-methyl-2,3-epoxybutane, and 1-chloro-2,3-dimethyl-2,3-epoxy-butane. More highly halogenated monoalkylene oxides are also useful in the present invention. Representative examples of these materials include 1,1-dichloro-2,3-epoxypropane, 1,1,1-trichloro-2,3-epoxypropane, 1-bromo-1,1-dichloro-2,3-epoxypropane, 1,1-dichloro-1-fluoro-2,3-epoxypropane, 1,1-difluoro-1-chloro-2,3-epoxypropane, etc. Still other useful haloalkylene oxides include 1,1-dichloro-2-methyl-2,3-epoxypropane, 1,1,1-trichloro-3,4-epoxybutane, 1,1-dichloro-3,4-epoxybutane, 1,1,1,2,2-pentachloro-3,4-epoxybutane, 1,1,1,4,4-pentachloro-2,3-epoxybutane, 1,1,1,2,2-mixed pentahalo-3,4-epoxybutane and 1,1,1,2,2-pentachloro-2-methyl-2,3-epoxybutane. Tetrachloroepoxybutanes such as 1,1,4,4-tetrachloro-2,3-epoxybutane, 1,1,2,2-tetrachloro-3,4-epoxybutane and 1,1,1,2-tetrachloro-3,4-epoxybutane may also be used.

Mixtures of any of the foregoing haloalkylene oxides can be used as well as mixtures of at least one haloalkylene oxide with up to about 50% by weight of one or more non-halogenated alkylene oxides. Exemplary of useful non-halogenated alkylene oxides are propylene oxide, 1-hexylene oxide, cyclohexane oxide, styrene oxide, methyl glycidyl ether and phenyl glycidyl ether.

By controlling the proportions of alkylene oxide yto hydroxyl-containing material, it is possible to limit the degree of addition and, consequently, the molecular weight of the polyols of the invention. Thus, the molar ratio of alkylene oxide material to hydroxyl group in said hydroxyl-containing material may be in the range of about 1:1 to 50:1, preferably the molar ratio is in the range of about 1:1 to 20:1.

Catalyst systems useful in the present invention comprise (i) a fluorinated acid selected from the group described above and (ii) a polyvalent tin compound as is described above. As little as about 0.05% by weight of the catalyst system based on the combined weight of the hydroxyl-containing material and alkylene oxide is effective in providing the polyols of the invention.

As discussed above the molar ratio of the polyvalent tin compound to the fluorinated acid is dependent upon which fluorinated acid is employed in the catalyst system. However, whatever the exact ratio used is, the catalyst system may be easily prepared by simply adding each of the ingredients to the polymerization mixture.

As has been previously stated, the fluorinated acid useful in the catalyst system is selected from the group consisting of bis(fluorinated aliphatic sulfonyl) alkanes, HF, and acids of the formula $H_mXF_{n+m}$. The bis(fluorinated aliphatic sulfonyl) alkanes are preferably highly fluorinated alkanes containing from 1 to about 15 carbon atoms. Additionally they include compounds which liberate such alkanes in the presence of heat or moisture. For example, bis(highly fluorinated alkylsulfonyl)alkanes, upon hydrolysis, will yield bis(highly fluorinated alkylsulfonyl)alkanes.

As it is used herein, the term highly fluorinated aliphatic radical encompasses fluorinated, saturated, monovalent, aliphatic radicals having 1 to 10 carbon atoms. The skeletal chain of the radical may be straight, branched or, if sufficiently large (e.g., at least 3 or 4 atoms), cycloaliphatic. Moreover, the skeletal chain may be interrupted by divalent oxygen atoms or trivalent nitrogen atoms bonded only to carbon atoms. Preferably, the chain of the fluorinated aliphatic radical does not contain more than one hetero atom (i.e., nitrogen or oxygen) for every two carbon atoms in the skeletal chain. A fully fluorinated group is preferred, but hydrogen or chlorine atoms may be present as substituents in the fluorinated aliphatic radical provided that not more than one atom of either is present in the radical for each carbon atom. Preferably, the fluoroaliphatic radical is a saturated perfluroalkyl radical having a skeletal chain that is straight or branched and has the formula $C_xF_{2x+1}$—wherein x has a value of from 1 to 18.

The preferred bis(fluorinated aliphatic sulfonyl) alkanes are those compounds having the formula

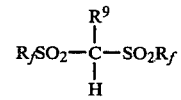

wherein each $R_f$ group is the same or different and is a fluorinated (preferably a highly fluorinated or perfluorinated) alkyl group containing from about 1 to 10 carbon atoms and $R^9$ is selected from hydrogen, halogen, alkyl groups having from 1 to about 10 (preferably 1 to 4) carbon atoms, alkenyl groups containing from about 1 to 3 carbon atoms, aryl groups (e.g., phenyl, naphthyl) and alkaryl groups of up to 10 carbon atoms. The alkyl, aryl and alkaryl may, if desired, be substituted by one or more constituents selected from halogen, highly fluorinated alkyl sulfonyl groups, carboxyl groups, alkoxycarbonyl groups, nitro groups, alkoxy groups and acetoxy groups.

Fully fluorinated groups are preferred, but hydrogen or chlorine atoms may be present as substituents in the group provided that not more than one atom of either is present in the radical for every two carbon atoms. The alkyl groups generally contain not more than 10 carbon atoms and preferably they contain less than 8 carbon atoms. Most preferably they contain up to 4 carbon atoms.

Representative examples of useful bis(perfluoroalkylsulfonyl) alkanes are: bis(trifluoromethylsulfonyl) methane, bis(difluorochloromethylsulfonyl)methane, tris(trifluoromethylsulfonyl)methane, bis(trifluoromethylsulfonyl)-4-bromophenylmethane, bis(trifluoromethylsulfonyl)-2-thienylmethane, bis(trifluoromethylsulfonyl)chloromethane, bis(trifluoromethylsulfonyl)benzylmethane, bis(trifluoromethylsulfonyl)phenylmethane, bis(trifluoromethylsulfonyl)-1-naphthylmethane, bis(perfluorobutylsulfonyl)methane, bis (2,2,3,3,4,4,4-heptafluorobutylsulfonyl)methane, perfluorobutylsulfonyltrifluoromethylsulfonylmethane, 1,2,2,3,3,4,4,4-heptafluorobutyltrifluoromethylsulfonylmethane, ethyl-6,6-bis (perfluoromethylsulfonyl)-4-bromohexanoate, methyl-4,4-bis(perfluoromethylsulfonyl)-2-carbomethoxy-2-bromobutanoate, ethyl-4,4-bis(perfluoromethylsulfonyl)-2-carboethoxy-2-nitrobutanoate, 1,1,3,3-tetra(trifluoromethylsulfonyl)propane, and 1,1-bis(trifluoromethylsulfonyl)octadecane.

Representative examples of useful bis(fluorinated aliphatic sulfonyl)alkanes are also described in U.S. Pat. Nos. 3,632,843; 3,704,311; 3,701,408; 3,776,960 and 3,794,687 which are incorporated herein by reference.

Another class of fluorinated acids useful in the present invention are substantially fully fluorinated and have the formula $H_nXF_{m+n}$ wherein X is sleected from the group consisting of boron, phosphorous, arsenic and antimony; m is 0 or 1 and n is 3 when X is boron and n is 5 when X is phosphorous, arsenic and antimony. Specific examples of useful fluorinated acids of this type are $BF_3$, $HBF_4$, $SbF_5$, $HSbF_6$, $PF_5$, $HPF_6$, $AsF_5$ and $HAsF_6$.

The polyvalent tin compounds useful in the catalyst system of the present invention have the formula

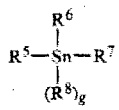

wherein $R^5$, $R^6$, $R^7$, $R^8$ and g are each as described above. Specific examples of polyvalent tin compounds of this type include diphenyl dibutyl tin, divinyl dibutyl tin, diallyl dibutyl tin, tributyl tin fluoride, triphenyl tin acetate, dibutyl tin oxide, and bis(tributyl tin oxide).

As has been stated, the chloroalkylene ether polyols of the present invention are optically clear and substantially colorless as is demonstrated by their color magnitude (i.e., they have a color magnitude of less than about 10). Color magnitude represents the deviation of the color of a given material from the color of distilled water when both colors are measured at about 25° C. The color of the water and of the samples is measured by a Hunterlab Model D25-4 Color Difference Meter available from Hunder-Associates Laboratory, 9529 Lee Highway, Fairfax, Va. The meter measures three parameters which characterize the color of a sample. These parameters are (i) the gray component "L" of the sample; (ii) the red-green component "a" of the sample (a plus value indicating redness and a minus value indicating greenness); and (iii) the yellow-blue component "b" of the sample (a plus value indicating yellowness and a minus value indicating blueness). The color magnitude (E) is calculated from the formula $$\Delta E = \sqrt{(L)^2 + (a)^2 + (b)^2}$$

wherein L, $\Delta a$ and $\Delta b$ respectively represent the difference between the L, a and b values of distilled water and the sample being tested. Distilled water has a color magnitude of 0 at 25° C.

Color magnitude values of less than about 10 represent optically clear and substantially colorless materials. The color of a material having a color magnitude of 10 is very light yellow and a thin film of such a material remains optically clear. As the color magnitude increases (i.e., as $\Delta E$ increases) the color and the optical clarity of the sample decreases. Thus, at a color magnitude of 20 the material has light brown color and a thin film thereof has a hazy optical clarity. At a color magnitude of 50 the material has a very dark brown color and a thin film thereof is difficult to see through The invention is further illustrated by means of the following examples wherein the term "parts" refers to parts by weight unless otherwise indicated. In the examples the poly(alkylene ether)polyols were prepared according to the following general procedure.

The polyethers were prepared in a glass reaction flask which was equipped with a stirrer, thermometer and a dropping funnel. A dry atmosphere was maintained within the flask during the reaction.

In each preparation the hydroxyl-containing material (ethylene glycol, 62.0 g, 1 mole) and the catalyst system were charged to the flask and stirred and heated to about 40°-60° C. The composition and quantity of the catalyst system was varied in each reaction. The haloalkylene oxide (epichlorohydrin or epibromohydrin) was then slowly charged to the stirred mixture over a period of about 3 hours. The reaction was allowed to proceed until it was substantially complete. The temperature of the reaction mixture was maintained between about 40° and 85° C. The amount of halohydrin employed was varied so as to control the hydroxyequivalent weight of the product. Thus, for example, 938 g (10.1 moles) of epichlorohydrin were employed in order to provide a product having a theoretical hydroxyl equivalent weight of about 500. On the other hand 1938 g (21 moles) of epichlorohydrin were employed in order to provide a product having a theoretical hydroxyl equivalent weight of about 1000.

EXAMPLES 1-25

Examples 1-25 represent a number of poly(chloroalkylene ether)polyols prepared according to the above-described general procedure utilizing both prior art catalyst systems and catalyst systems of the invention. The exact nature of the catalyst system utilized and the results obtained are given in Table 1.

The catalyst system utilized in Examples 1-3 was $BF_3$; that in Example 4 was $HSbF_6 \cdot H_2O$; that in Example 5 was $(C_2H_5)_3O^+PF_6^-$ and that in Example 6 was $SbF_5$. As can be seen the poly(chloroalkylene ether)polyols prepared from these catalyst systems were darkly colored as is demonstrated by their high $\Delta E$ values (i.e., between 30 and 52).

Examples 7-9 demonstrate the effect of the individual components of the catalyst system of the present invention upon the poly(chloroalkylene ether )polyols produced. Thus, in Example 7 the catalyst system was a polyvalent tin compound of the formula

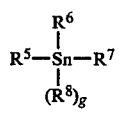

(i.e., $(C_6H_5)_2Sn(C_4H_9)_2$. As can be seen from Example 7 there was no reaction even after 5 hours of mixing when the diphenyl dibutyl tin compound was used as the catalyst system. When the catalyst system was the sulfonyl alkane compound (Examples 8 and 9) darker products than those of the invention were obtained as is shown by their color magnitude.

Examples 10–12 demonstrate the criticality of the molar ratio of the fluorinated acid of the formula $H_mXF_{m-n}$ to the tin compound in the catalyst composition of the invention. Thus in Examples 10 and 11 the ratio was 1:1 and 1.1:1. In each case the resulting product was very dark brown (i.e., $\Delta E$ of 53.1 and 52.9 respectively). However, in Example 12 the molar ratio was 1.13:1 and the resulting product was optically clear and substantially colorless (i.e., a color magnitude of 2.1).

Examples 13–24 demonstrate the present invention. In each of these examples an optically clear and substantially colorless poly(chloroalkylene ether)polyol was obtained. This is demonstrated by the low E values obtained (i.e., $\Delta E$ less than about 5). Examples 13–16 show the effect of varying the molar ratio of the $H_mXF_{m+n}$ fluorinated acid to the polyvalent tin compound. Examples 17–20 show the use of the bis(-fluorinated aliphatic sulfonyl)alkanes and the use of the varying ratios of this acid to the tin compound in the catalyst system. Examples 21–24 show the use of differing tin compounds in the catalyst system. Example 25 shows that highly halogenated alkyleneoxides (e.g., 1,1,1-trichlorobutylene oxide) can also be used in the present invention.

EXAMPLES 26–27

A series of hydroxyl-terminated poly(haloalkylene ethers) were prepared as described in the general procedure. The resultant polyethers were tested for initial color magnitude then subjected to heat (80° C.) for 14 hours after which time the polyethers were tested for final color magnitude. Example 26 was performed using a sample from the polyol prepared in Example 13 of Table 1. Example 27 was performed using a 490 hydroxyl equivalent weight polyether prepared according to the general procedure but employing $(C_2H_5)_3O^+PF_6^-$ (0.2% by weight of the combined weight of the ethylene glycol and the epichlorohydrin) as the catalyst system.

TABLE 2

| EXAMPLE | $\Delta E_I$ | $\Delta E_F$ |
|---|---|---|
| 26 | 1.51 | 1.56 |
| 27 | 18.55 | 30.41 |

$\Delta E_I$ is the initial color of the polyol in the test. $\Delta E_F$ is the color of the polyol after heat aging at 80° C. for a 14 hour period. The behavior of Example 26 is characteristic of all the polyols of the invention. As can be seen, poly-(chloroalkylene ether)polyols of the invention exhibit essentially no change in color magnitude while prior art poly(chloroalkylene ether)polyols darken dramatically in color.

EXAMPLES 28–34

A series of polyurethanes were made using various poly(chloroalkylene ether)polyols, and a polyfunctional polyisocyanate. The polyols were prepared as described in the general procedure. The polyfunctional isocyanate was "Mondur MRS" (a polymethylene polyphenyl isocyanate having an average of about 2.6 isocyanate

TABLE 1

| EX. | CATALYST SYSTEM A | B | MOLAR RATIO B/A | QUANTITY[a] % A | % B | CONVERSION (%) | NO EQ. WT. CALC | FOUND | MOLECULAR COLOR WT $\bar{M}_n$ | $\bar{M}_w$ | $\Delta E$ | RXN TIME Hours |
|---|---|---|---|---|---|---|---|---|---|---|---|---|
| 1 | $BF_3$ | | | 0.30 | | 99 | 500 | 496 | 863 | 1040 | 52.6 | 6 |
| 2 | $BF_3$ | | | 0.10 | | 99 | 1020 | 930 | 1420 | 1040 | 50.4 | 6 |
| 3 | $BF_3$ | | | 0.10 | | 99 | 275 | 252 | 542 | 589 | 43.5 | 6 |
| 4 | $HSbF_6 \cdot 6H_2O$ | | | 0.10 | | 99 | 491 | 450 | 854 | 1050 | 51.6 | 6 |
| 5 | $(C_2H_5)_3O^+PF_6^-$ | | | 0.20 | | 99 | 500 | 426 | 882 | 1180 | 36.8 | 6 |
| 6 | $SbF_5$ | | | 0.10 | | 99 | 1020 | 950 | 1210 | 2060 | 31.7 | 6 |
| 7 | | $(C_6H_5)_2Sn(C_4H_9)_2$ | | 0.0 | 0.224 | 0 | No reaction | | | | | 5 |
| 8 | $(CF_3SO_2)_2CH_6H_5$ | | | 0.50 | 0.0 | 81 | 810 | 665 | 1070 | 1570 | 12.6 | 24 |
| 9 | $(CF_3SO_2)_2CHC_6H_5$ | | 0.50 | 0.0 | 93.7 | 470 | 410 | 815 | 958 | 10.5 | 24 | |
| 10 | $HSbF_6 \cdot 6H_2O$ | $(C_6H_5)_2Sn(C_4H_9)_2$ | 1:1 | 0.10 | 0.118 | 99 | 490 | 420 | 884 | 1070 | 53.1 | 5 |
| 11 | $HSbF_6 \cdot 6H_2O$ | $(C_6H_5)_2Sn(C_4H_9)_2$ | 1.1:1 | 0.10 | 0.124 | 99 | 490 | 425 | 921 | 1050 | 52.9 | 5 |
| 12 | $HSbF_66H_2O$ | $(C_6H_5)_2Sn(C_4H_9)_2$ | 1.13:1 | 0.10 | 0.127 | 99 | 490 | 437 | 896 | 1000 | 2.1 | 5 |
| 13 | $HSbF_6 \cdot 6H_2O$ | $(C_6H_5)_2Sn(C_4H_9)_2$ | 1.16:1 | 0.10 | 0.130 | 99 | 490 | 437 | 894 | 1000 | 1.5 | 5 |
| 14 | $HSbF_6 \cdot 6H_2O$ | $(C_6H_5)_2Sn(C_4H_9)_2$ | 1.51:1 | 0.10 | 0.17 | 99 | 490 | 450 | 883 | 1010 | 2.2 | 5 |
| 15 | $HSbF_6 \cdot 6H_2O$ | $(C_6H_5)_2Sn(C_4H_9)_2$ | 2.0:1 | 0.10 | 0.224 | 99 | 490 | 470 | 860 | 993 | 0.8 | 5 |
| 16 | $HSbF_6 \cdot 6H_2O$ | $(C_6H_5)_2Sn(C_4H_9)_2$ | 2.65:1 | 0.10 | 0.298 | 99 | 490 | 433 | 827 | 967 | 1.8 | 5 |
| 17 | $(CF_3SO_2)_2CHC_6H_5$ | $(C_6H_5)_2Sn(C_4H_9)_2$ | 0.195:1 | 0.30 | 0.064 | 93 | 465 | 452 | 883 | 1020 | 3.6 | 10 |
| 18 | $(CF_3SO_2)_2CHC_6H_5$ | $(C_6H_5)_2Sn(C_4H_9)_2$ | 0.392:1 | 0.30 | 0.128 | 99.5 | 496 | 470 | 939 | 1025 | 2.1 | 5 |
| 19 | $(CF_3SO_2)_2CHC_6H_5$ | $(C_6H_5)_2Sn(C_4H_9)_2$ | 0.785:1 | 0.30 | 0.256 | 99 | 491 | 478 | 924 | 1046 | 2.5 | 3 |
| 20 | $(CF_3SO_2)_2CHC_6H_5$ | $(C_6H_5)_2Sn(C_4H_9)_2$ | 1.96:1 | 0.30 | 0.64 | 95.2 | 476 | 450 | 923 | 1025 | 2.2 | 5 |
| 21 | $(CF_3SO_2)_2CHC_6H_5$ | $(C_6H_5)_3SnAc$ | 1:1 | 0.30 | 0.34 | 95 | 476 | 450 | 839 | 978 | 2.5 | 3 |
| 22 | $(CF_3SO_2)_2CHC_6H_5$ | $(C_4H_9)_3SnF$ | 1:1 | 0.30 | 0.25 | 99 | 496 | 470 | 887 | 1023 | 3.5 | 4 |
| 23 | $(CF_3SO_2)_2CHC_6H_5$ | $(C_4H_9)_2SN(C_2H_3)_2$ | 1:1 | 0.30 | 0.241 | 99 | 491 | 468 | 870 | 995 | 1.6 | 6 |
| 24 | $HBF_4$ | $(C_6H_5)_2Sn(C_4H_9)_2$ | 2.0:1 | 0.15 | 1.3 | 99 | 490 | 472 | 865 | 998 | 2.1 | 10 |
| 25 | [b]$HSbF_6 \cdot 6H_2O$ | $(C_6H_5)_2Sn(C_4H_9)_2$ | 2.0:1 | 0.10 | 0.224 | 99 | 322 | 318 | 622 | 645 | 5.1 | 24 |

[a]Percentages are percentages by weight of the combined weight of the ethylene glycol and the epichlorohydrin.
[b]1,1,1-trichlorobutylene oxide was substituted for epichlorohydrin in this example.

roups per molecule and being available from Mobay Company).

The polyurethanes were prepared by combining the ingredients in a suitable reaction vessel and stirring them for 1-2 minutes at a temperature of about 25° C. A moisture free atmosphere was maintained in the reaction vessel. There was no catalyst added to promote the reaction.

Examples 28 and 29 utilized poly(chloroalkylene ether)polyols according to the invention. These polyols were prepared using the same catalyst system and amounts thereof as are set forth in Example 15. The polyol employed in Example 28 had a theoretical hydroxyl-equivalent weight of 325 while the polyether employed in Example 29 had a theoretical hydroxyl equivalent weight of 500.

Examples 30-34 utilized poly(chloroalkylene ether)polyols prepared from prior art catalyst systems. The polyol employed in Example 30 had a theoretical hydroxyl equivalent weight of 1000 and was prepared utilizing $BF_3$ (0.3% by weight of the combined weight of the epichlorohydrin and the ethylene glycol) as the catalyst system. The polyols employed in Examples 31 and 32 had theoretical hydroxyl equivalent weights of 500 and 325 respectively and were prepared utilizing $(C_2H_5)_3O^+PF_6^-$ (0.2% by weight of the epichlorohydrin and the ethylene glycol) as the catalyst system. The polyols employed in Examples 33 and 34 had theoretical hydroxyl equivalent weights of 500 and 325 respectively and were prepared with $HSbF_6.6H_2O$ (0.1% by weight of the combined weight of the epichlorohydrin and the ethylene glycol) as the catalyst system.

The results of the preparations are given in Table 3. As can be seen the polyurethanes of Examples 28 and 29 prepared with the poly(chloroalkylene ether)polyols of the invention) gelled quickly while the polyurethanes of Examples 30-34 (prepared with prior art poly(chloroalkylene ether)polyols, did not gel even after 24 hours. Moreover the polyurethanes of Examples 28-29 cured within 24 hours while those of Examples 30-34 did not cure even after 3 days.

TABLE 3

| EXAMPLE | NCO/OH | POLYURETHANE VISCOSITY (cps) | |
|---|---|---|---|
| | | INITIAL (Time = 0 hours) | FINAL (Time = 24 hours) |
| 28 | 1.2:1 | 4800 | Gelled within* |

TABLE 3-continued

| EXAMPLE | NCO/OH | POLYURETHANE VISCOSITY (cps) | |
|---|---|---|---|
| | | INITIAL (Time = 0 hours) | FINAL (Time = 24 hours) |
| 29 | 1.2:1 | 2200 | 15 minutes Gelled within* 15 minutes |
| 30 | 1.2:1 | 5900 | 24000 |
| 31 | 1.2:1 | 5900 | 16000 |
| 32 | 1.2:1 | 2300 | 5400 |
| 33 | 1.2:1 | 4800 | 15000 |
| 34 | 1.2:1 | 2200 | 27000 |

*Gellation occurs when the viscosity > 1,000,000 cps.

EXAMPLES 35-40

A series of hydroxyl-terminated poly(chloroalkylene ethers) according to the invention were prepared according to the general procedure except that various hydroxyl-containing materials were substituted for ethylene glycol. In each of these examples the catalyst system comprised 0.1% $HSbF_6.6H_2O$ and 0.224% diphenyl dibutyl tin (both percentages being percentages by weight of the combined weight of the hydroxyl material and the epichlorohydrin. The resulting polyols were then tested for percent conversion, hydroxyl equivalent weight and color magnitude. The exact ingredients used to prepare the polyols, the amounts of each and the results obtained are reported in Table 4.

TABLE 4

| | HYDROXYL-CONTAINING MATERIAL | | EPICHLOROHYDRIN PARTS BY WGT | % CONVERSION | HYDROXYL EQ. WT. | | |
|---|---|---|---|---|---|---|---|
| EXAMPLE | TYPE | PARTS BY WGT | | | THEORETICAL | FOUND | ΔE |
| 35 | $CH_3CH_2OH$ | 46 | 954 | 98.5 | 1000 | 894 | 2.9 |
| 36 | $HO(CH_2)_6OH$ | 118 | 882 | 99.7 | 500 | 427 | 2.2 |
| 37 | 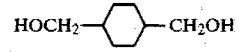 | 144 | 855 | 99.5 | 500 | 445 | 1.01 |
| 38 | $C_2H_5C(CH_2OH)_3$ | 134 | 1366 | 98.7 | 500 | 439 | 2.5 |
| 39 |  | 198 | 802 | 99.5 | 500 | 424 | 3.1 |
| 40 | 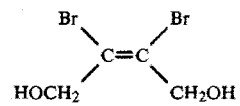 | 246 | 758 | 99.4 | 500 | 446 | 5.2 |

EXAMPLE 41

A hydroxyl-terminated poly(bromoalkylene ether) according to the invention was prepared. A mixture of cyclohexanedimethanol (72 g, MW 144, 0.5 moles) and methylene chloride (500 ml) was heated to 40° C. and the catalyst system (48% aqueous fluoboric acid and 1.8 g of diphenyl dibutyl tin) 3.8 g was added. Epibromohydrin (purified by distillation, 528 g) was then added slowly over a period of one hour into the mixture and the reaction temperature was maintained at 40°-45° C. The mixture was allowed to stir at 40° C. for 16 hours after which 58% ammonium hydroxide was added and stirred until the mixture reached a pH=7. Anhydrous magnesium sulfate and Celite® were added slowly, stirred and filtered. The solvent and residual epibromohydrin were removed under vacuum. A 96% yield of a yellowish polyepibromohydrin was obtained.

It had a hydroxyl equivalent weight of 358, a weight average molecular weight of 1023, a number average molecular weight of 817 and a bromine content of 46.7%.

EXAMPLE 42

A hydroxyl terminated poly(chloroalkylene ether) according to the invention was prepared. A mixture of cyclohexane dimethanol (36 g, MW 144, 0.25 moles) and the catalyst system (0.31 g of 48% aqueous hydrofluoric acid and 0.17 g of diphenyl dibutyl tin) was heated to 60°-65° C. Epichlorohydrin (214 g, 2.31 moles) was added slowly to the mixture while maintaining the same temperature. The reaction mixture was allowed to stir for an additional 16 hours. Vacuum distillation provided a yield of 72% of colorless and slightly cloudy poly(chloroalkylene ether) according to the invention. The product had a hydroxyl equivalent weight of 332, a weight average molecular weight of 838, and a color magnitude of 1.69.

The yield of the chloroalkylene ether may be improved to 97.3% by utilizing a catalyst system of 0.75 g of 48% aqueous hydrofluoric acid and 0.5 g of diphenyl dibutyl tin. The product obtained from this reaction has a hydroxyl equivalent weight of 407.

What is claimed is:

1. A method for the preparation of hydroxyl-terminated poly(haloalkylene ethers) which comprises reacting a hydroxyl material containing from about 1 to 6 hydroxyl groups and a haloalkylene oxide in the presence of a catalytic amount of a catalyst system comprising (i) a fluorinated acid selected from the group consisting of bis(fluorinated aliphatic sulfonyl protonic)alkanes, HF and acids of the formula $H_mXF_{n+m}$ wherein X is selected from the group consisting of boron, phosphorous arsenic and antimony; m is 0 or 1; n is 3 when X is boron and n is 5 when X is phosphorous, arsenic and antimony; and (ii) a polyvalent tin compound having the formula

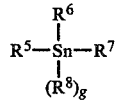

wherein
   g is 0 or 1;
   $R^5$ and $R^6$ are the same or different and are selected from saturated and unsaturated aliphatic and aromatic hydrocarbyl groups containing from 1 to about 10 carbon atoms;
   $R^7$ is selected from the group consisting of oxygen and saturated and unsaturated aliphatic and aromatic hydrocarbyl groups containing from 1 to about 10 carbon atoms, provided that when $R^7$ is oxygen then g is 0; and
   $R^8$ is selected from the group consisting of fluorine, acyloxy groups containing less than about 10 carbon atoms, saturated aliphatic hydrocarbyl groups containing from 1 to about 10 carbon atoms and

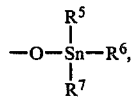

provided that when $R^5$, $R^6$, and $R^7$ are each saturated aliphatic hydrocarbyl groups then $R^8$ is selected from the group consisting of fluorine, acyloxy groups containing less than about 10 carbon atoms and

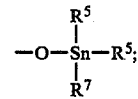

provided that when said fluorinated acid is said bis(fluorinated aliphatic sulfonyl)alkane, the molar ratio of said polyvalent tin compound to said bis(fluorinated aliphatic sulfonyl)alkane is in the range of about 0.2:1 to 2:1; and
   provided further than when said fluorinated acid is selected from HF and acids of the formula $H_mXF_{n+m}$, the molar ratio of said polyvalent tin compound to said fluorinated acid is in the range of about 1.13:1 to 3:1.

2. A method according to claim 1 wherein said catalyst system comprises (i) said bis(fluorinated aliphatic sulfonyl)alkane and (ii) polyvalent tin compound.

3. A method according to claim 2 wherein said polyvalent tin compound is selected from the group consisting of diphenyl dibutyl tin, divinyl dibutyl tin, diallyl dibutyl tin, tributyl tin fluoride, triphenyl tin acetate, dibutyl tin oxide, and bis(tributyl tin oxide).

4. A method according to claim 2 wherein said bis(fluorinated aliphatic sulfonyl)alkane is selected from
bis(trifluoromethylsulfonyl)methane
bis(difluorochloromethylsulfonyl)methane
tris(trifluoromethylsulfonyl)methane
bis(trifluoromethylsulfonyl)-4-bromophenylmethane
bis(trifluoromethylsulfonyl)-2-thienylmethane
bis(trifluoromethylsulfonyl)chloromethane
bis(trifluoromethylsulfonyl)benzylmethane
bis(trifluoromethylsulfonyl)phenylmethane
bis(trifluoromethylsulfonyl)-1-naphthylmethane
bis(perfluorobutylsulfonyl)methane
bis(2,2,3,3,4,4,4-heptafluorobutylsulfonyl)methane
perfluorobutylsulfonyltrifluoromethylsulfonylmethane
1,2,2,3,3,4,4,4-heptafluorobutyltrifluoromethylsulfonylmethane
ethyl 6,6-bis(perfluoromethylsulfonyl)-4-bromohexanoate
methyl 4,4-bis(perfluoromethylsulfonyl)-2-carbomethoxy-2-bromobutanoate
ethyl 4,4-bis(perfluoromethylsulfonyl)-2-carboethoxy-2-nitrobutanoate
1,1,3,3-tetra(trifluoromethylsulfonyl)propane and
1,1-bis(trifluoromethylsulfonyl)octadecane.

5. A method according to claim 1 wherein said catalyst system comprises (i) said fluorinated acid selected from HF and acids of the formula $H_mXF_{n+m}$ and (ii) said polyvalent tin compound.

6. A method according to claim 5 wherein said polyvalent tin compound is selected from the group consisting of diphenyl dibutyl tin, divinyl dibutyl tin, diallyl dibutyl tin, tributyl tin fluoride, triphenyl tin acetate, dibutyl tin oxide, and bis(tributyl tin oxide).

7. A method according to claim 6 wherein said fluorinated acid has the formula $H_mXF_{n+m}$ and is selected from the group consisting of $BF_3$, $HBF_4$, $SbF_5$, $HSbF_6$, $PF_5$, $HPF_6$, $AsF_5$ and $HAsF_6$.

8. A method according to claim 5 wherein said fluorinated acid is HF.

* * * * *

UNITED STATES PATENT AND TRADEMARK OFFICE
CERTIFICATE OF CORRECTION

PATENT NO. : 4,431,845
DATED : February 14, 1984
INVENTOR(S) : Chung I. Young and Loren L. Barber, Jr.

It is certified that error appears in the above-identified patent and that said Letters Patent is hereby corrected as shown below:

The title "METHOD FOR THE PREPARATION OF 1-HYDROXYL-TERMINATED POLY(HALOALKYLENE ETHERS) should read --METHOD FOR THE PREPARATION OF HYDROXYL-TERMINATED POLY(HALOALKYLENE ETHERS)--.

Col. 4, line 57, "predent" should read --present--.

Col. 5, line 55, "yto" should read "to".

Col. 7, line 26, "sleected" should read --selected--.

Signed and Sealed this

Twenty-sixth Day of March 1985

[SEAL]

Attest:

DONALD J. QUIGG

Attesting Officer

Acting Commissioner of Patents and Trademarks